United States Patent
Matsushita et al.

(10) Patent No.: US 10,209,375 B2
(45) Date of Patent: Feb. 19, 2019

(54) X-RAY DATA PROCESSING APPARATUS, X-RAY DATA PROCESSING METHOD, AND X-RAY DATA PROCESSING PROGRAM

(71) Applicant: Rigaku Corporation, Akishima-shi, Tokyo (JP)

(72) Inventors: Kazuyuki Matsushita, Tokyo (JP); Takuto Sakumura, Tokyo (JP); Yasukazu Nakaye, Tokyo (JP)

(73) Assignee: RIGAKU CORPORATION, Akishima-Shi (JP)

( * ) Notice: Subject to any disclaimer, the term of this patent is extended or adjusted under 35 U.S.C. 154(b) by 866 days.

(21) Appl. No.: 14/163,608

(22) Filed: Jan. 24, 2014

(65) Prior Publication Data
US 2014/0236523 A1    Aug. 21, 2014

(30) Foreign Application Priority Data

Feb. 19, 2013   (JP) .................................. 2013-029782

(51) Int. Cl.
*G01T 7/00*     (2006.01)
*G01T 1/29*     (2006.01)
*G01N 23/087*   (2018.01)

(52) U.S. Cl.
CPC ......... *G01T 1/2914* (2013.01); *G01N 23/087* (2013.01); *G01T 7/005* (2013.01)

(58) Field of Classification Search
CPC ...... G01T 1/2914; G01T 7/005; G01N 23/087
See application file for complete search history.

(56) References Cited

U.S. PATENT DOCUMENTS 5,491,738 A * 2/1996 Blake ................... G01N 23/207
                                                   378/49
6,002,741 A * 12/1999 Eisen ...................... G01T 1/247
                                                   250/370.01
(Continued)

FOREIGN PATENT DOCUMENTS

JP        S63-171387 A      7/1988
JP        2502555 B2  *     5/1996
(Continued)

OTHER PUBLICATIONS

Mathieson, K, et al., Charge sharing in silicon pixel detectors, Nuclear Instruments and Methods in Physics Research A, 487 (2002) 113-122.*

(Continued)

*Primary Examiner* — Alexander Satanovsky
*Assistant Examiner* — Lina M Cordero
(74) *Attorney, Agent, or Firm* — Birch, Stewart, Kolasch & Birch, LLP

(57) ABSTRACT

An X-ray data processing apparatus for processing X-ray data that is obtained by simultaneously measuring X-rays of multiple wavelengths. The apparatus includes a management unit 210 to receive and manage X-ray data that is detected by a detector, a calculation unit 230 which calculates a detection amount of charge sharing events in lower energy side data caused by higher energy X-ray, based on the higher energy side data obtained using a threshold value on a higher energy side and the lower energy side data obtained using a threshold value on a lower energy side of the received X-ray data, and a correction unit 250 to reconfigure the lower energy side data using the calculated detection amount. The apparatus can remove a residual image of an X-ray on a higher energy side which remains in data on a lower energy side.

6 Claims, 17 Drawing Sheets

(56) References Cited

U.S. PATENT DOCUMENTS

| | | | |
|---|---|---|---|
| 6,389,102 B2* | 5/2002 | Mazor | G01N 23/20 250/208.1 |
| 6,559,453 B2 | 5/2003 | Lundqvist | |
| 7,208,739 B1* | 4/2007 | Yanoff | G01T 1/171 250/363.09 |
| 7,486,764 B2* | 2/2009 | Tkaczyk | G01T 1/249 250/370.09 |
| 8,300,767 B1 | 10/2012 | Matsushita et al. | |
| 8,373,135 B2* | 2/2013 | Kappler | G01T 1/247 250/336.1 |
| 2002/0179844 A1 | 12/2002 | Lundqvist | |
| 2010/0119040 A1* | 5/2010 | Suyama | G01T 1/00 378/62 |
| 2010/0215230 A1* | 8/2010 | Bornefalk | G06T 11/005 382/128 |
| 2011/0051901 A1* | 3/2011 | Michel | G01T 1/026 378/165 |
| 2011/0311022 A1 | 12/2011 | Kappler | |
| 2011/0317813 A1 | 12/2011 | Matsushita et al. | |
| 2012/0112088 A1* | 5/2012 | Abraham | G01T 1/171 250/395 |
| 2012/0269322 A1 | 10/2012 | Matsushita et al. | |
| 2013/0110438 A1* | 5/2013 | Rinkel | G01N 23/087 702/85 |

FOREIGN PATENT DOCUMENTS

| | | | |
|---|---|---|---|
| JP | 2011089901 A | * | 5/2011 |
| JP | 2012-13463 A | | 1/2012 |

OTHER PUBLICATIONS

Takoukam P., Investigation of photon counting pixel detectors for X-ray spectroscopy and imaging, Doctoral Thesis, Apr. 2011.*
JP-2011089901-A translation (Year: 2011).*
Nakajima et al., "Evaluation Test of Broadband X-ray Imaging Spectrograph (XRPIX1) Using SOI Techniques and Study on Performance Improvement", Division of Physics and Astronomy, Graduate School of Science, Kyoto University, Department of Physics and Department of Astronomy, Faculty of Science, Japan, Jan. 27, 2011, 12 pages.

* cited by examiner

X-RAY DATA PROCESSING APPARATUS, X-RAY DATA PROCESSING METHOD, AND X-RAY DATA PROCESSING PROGRAM

FIELD OF THE INVENTION

The present invention relates to X-ray data processing apparatuses, X-ray data processing methods, and X-ray data processing programs for processing the X-ray data that is obtained by simultaneously measuring X-rays of multiple wavelengths.

DESCRIPTION OF THE RELATED ART

In recent years, techniques for simultaneously measuring diffraction X-rays using X-ray sources of multiple wavelengths are under study (e.g., see Patent Document 1). The wavelength discrimination X-ray diffractometer described in Patent Document 1 irradiates a sample with characteristic X-rays of different wavelengths of Mo radiation, Cu radiation, and the like generated from X-ray generation sources, and detects the characteristic X-rays diffracted by the sample with an X-ray detector. Each pixel of this X-ray detector receives the X-ray, and outputs a pulse signal corresponding to the wavelength of the X-ray, and a discrimination circuit discriminates the output signal of the pixel for each wavelength of the characteristic X-ray and outputs the resulting signal.

On the other hand, it is known that charge sharing occurs when an X-ray is detected by a plurality of pixels. The charge sharing refers to a phenomenon that a tail is generated on a lower energy side by the generated charges spanning a plurality of pixels. Conventionally, in order to minimize the effect of such charge sharing, attempts have been made to eliminate the charge sharing by improving hardware side, such as by using a detector having a sensor provided with a groove or a TSV (Through Silica Via) or by using a detector that determines for each incidence event with a reduced count rate. In a general methodology, the charge sharing is removed on hardware side because the charge sharing interrupts the measurement of an original X-ray energy.

Moreover, in using a detector that does not have an energy discrimination function and is unsuitable for the applications for receiving multiple wavelengths, a method has been proposed for avoiding the effect of charge sharing by using an intensity ratio with respect to a pixel around the obtained diffraction X-ray data (e.g., see Non-patent Document 1, pp. 64-67).

While for a zero-dimensional detector, a detector corresponding to a multiple wavelength input has been produced, because there is no adjacent detection unit, the zero-dimensional detector can separate multiple wavelength data based on a difference between the obtained X-ray diffraction data and is not affected by charge sharing.

PATENT DOCUMENT

[Patent Document 1]
Japanese Patent Application Laid-Open No. 2012-13463

NON-PATENT DOCUMENT

[Non-patent Document 1]
Shinya Nakajima, "Evaluation test of broadband X-ray imaging spectrograph (XRPIX) using SOI techniques and study on performance improvement", Kyoto University master thesis, Jan. 27, 2011.

When X-rays are measured simultaneously using X-ray sources of multiple wavelengths by the wavelength discrimination X-ray diffractometer described in Patent Document 1 as referred above, a plurality of pieces of data based on X-rays of different wavelengths can be simultaneously acquired by one measurement with respect to each pixel. Moreover, the data of diffraction X-rays of different wavelengths can be efficiently acquired using the whole region of a light receiving surface of a two-dimensional detector.

However, in attempting to analyze an X-ray on a lower energy side using such a measurement method, a residual image on a higher energy side remains due to the effect of charge sharing and thus high precision analysis cannot be performed. FIG. 13A and FIG. 13B show a diffraction image created by an Mo radiation source and a diffraction image created by a Cu radiation source which are obtained using the conventional method (measurement method described in Patent Document 1), respectively. In FIG. 13A, the diffraction image by the Cu radiation is not detected, while in FIG. 13B a residual image of a diffraction spot created by the Mo radiation remains overlapping with the diffraction image created by the Cu radiation. The residual image remains in this manner because an apparent intensity of an X-ray on a higher energy side increases in a lower energy region due to charge sharing and leaves a residual image in peripheral pixels.

Moreover, in attempting to remove the residual image using the related art, a pixel on which multiple wavelengths are simultaneously incident as diffraction X-rays cannot be processed. Therefore, the whole intensity will be lost as a result of subtracting a background corresponding to the residual image.

As described above, conventionally a detector comprising a plurality of detection portions each having an energy discrimination function has never been used in applications for receiving multiple wavelengths. Therefore, it is believed that data can be separated simply by subtracting the diffraction data obtained on a higher energy side from the diffraction data on a lower energy side. However, an image having a residual image is obtained because there is actually an influence of charge sharing.

In contrast, in the method for avoiding the effect of charge sharing using an intensity ratio with respect to a pixel around diffraction X-ray data, data cannot be separated by a single pixel. A detector for X-ray diffraction that accurately separates an incident multiple wavelength X-ray using one or more dimensional detector has not been put into practical use yet, and therefore a problem has not surfaced yet that incident multiple wavelengths cannot be accurately separated by such a detector.

SUMMARY OF THE INVENTION

The present invention has been made in view of the above circumstances, and provides an X-ray data processing apparatus, an X-ray data processing method, and an X-ray data processing program capable of removing a residual image of an X-ray on a higher energy side that remains in data on a lower energy side in detecting a multiple wavelength X-ray.

(1) In order to achieve the above-described purpose, the X-ray data processing apparatus of the present invention is an X-ray data processing apparatus for processing X-ray data that is obtained by simultaneously measuring X-rays of multiple wavelengths, the X-ray data processing apparatus comprising: a management unit configured to receive and manage X-ray data that is detected by a detector with a plurality of adjacent detection portions and separated by an energy threshold value; a calculation unit configured to calculate a detection amount of charge sharing events in lower energy side data which are caused by higher energy X-ray, based on the higher energy side data obtained using a threshold value on a higher energy side and the lower energy side data obtained using a threshold value on a lower energy side of the received X-ray data; and a correction unit configured to reconfigure the lower energy side data using the calculated detection amount.

In this manner, the detection amount caused by charge sharing can be canceled for each detection portion and a residual image of an X-ray on a higher energy side remaining in data on a lower energy side can be removed. As a result, also in measurement in which X-rays of multiple wavelengths are input, the accuracy of analysis compares favorably with the accuracy of analysis in single-wavelength measurement. Note that, the reconfiguration of the lower energy side data is performed, for example, by subtracting a detection amount of charge sharing events in lower energy side data which are caused by higher energy X-ray. The reconfiguring lower energy side data also includes performing fitting with respect to the whole higher energy side and lower energy side to directly calculate the detection amount on the lower energy side.

(2) In the X-ray data processing apparatus of the present invention, the calculation unit calculates, for each detection portion of the detector, a detection amount caused by charge sharing, from a ratio or a difference between the higher energy side data included in the lower energy side data and the lower energy side data.

Thus, the effect by charge sharing can be evaluated using a ratio or a difference between the lower energy side data and the higher energy side data. Moreover, an X-ray profile shape due to charge sharing can be reproduced taking a pixel shape and the like into consideration.

(3) In the X-ray data processing apparatus of the present invention, the calculation unit calculates, for each detection portion of the detector, a detection amount caused by charge sharing, with a probability corresponding to the detector and an incident X-ray wavelength.

Thus, the effect by charge sharing can be evaluated by calculation based on a formula. Moreover, an X-ray profile shape due to charge sharing can be reproduced taking a pixel shape and the like into consideration.

(4) In the X-ray data processing apparatus of the present invention, the calculation unit calculates, for each detection portion of the detector, a detection amount caused by charge sharing, using an actual measurement value prepared in advance. Thus, the probability that charges are generated can be evaluated corresponding to a detector and a peak present on a higher energy side, and the effect by charge sharing can be accurately calculated.

(5) In the X-ray data processing apparatus of the present invention, the calculation unit, when there are three or more types of incident X-ray energy, optimizes an accumulated error and calculates the detection amount caused by charge sharing. Thus, with regard to the measurement result by radiation sources of three or more wavelengths, the effect of charge sharing can be accurately evaluated.

(6) In the X-ray data processing apparatus of the present invention, the management unit manages X-ray diffraction data that is measured with an Mo radiation source and a Cu radiation source and separated by a threshold value for separating each radiation source, the calculation unit for the charge sharing portion calculates a detection amount caused by charge sharing which is linked with the Mo radiation source, and the correction unit subtracts the detection amount caused by charge sharing which is calculated from the X-ray diffraction data of the Cu radiation source. Thus, a result of simultaneously performing X-ray diffraction measurement with Mo and Cu used as the radiation sources can be accurately analyzed.

(7) The X-ray data processing method of the present invention is an X-ray data processing method for processing X-ray data that is obtained by simultaneously measuring X-rays of multiple wavelengths, the method comprising the steps of: receiving and managing X-ray data that is detected by a detector with a plurality of adjacent detection portions and separated by an energy threshold value; calculating a detection amount of charge sharing events in lower energy side data which are caused by higher energy X-ray, based on the higher energy side data obtained using a threshold value on a higher energy side and the lower energy side data obtained using a threshold value on a lower energy side of the received X-ray data; and reconfiguring the lower energy side data using the calculated detection amount. Thus, a residual image of the X-ray on a higher energy side remaining in data on a lower energy side can be removed.

(8) The X-ray data processing program of the present invention is an X-ray data processing program for processing X-ray data that is obtained by simultaneously measuring X-rays of multiple wavelengths, the program causing a computer to execute the processes of: receiving and managing X-ray data that is detected by a detector with a plurality of adjacent detection portions and separated by an energy threshold value; calculating a detection amount of charge sharing events in lower energy side data which are caused by higher energy X-ray, based on the higher energy side data obtained using a threshold value on a higher energy side and the lower energy side data obtained using a threshold value on a lower energy side of the received X-ray data; and reconfiguring the lower energy side data using the calculated detection amount. Thus, a residual image of the X-ray on a higher energy side remaining in data on a lower energy side can be removed.

According to the present invention, the detection amount caused by charge sharing can be calculated and a residual image of an X-ray on a higher energy side remaining in data on a lower energy side can be removed.

DETAILED DESCRIPTION OF THE INVENTION

Figure 1:
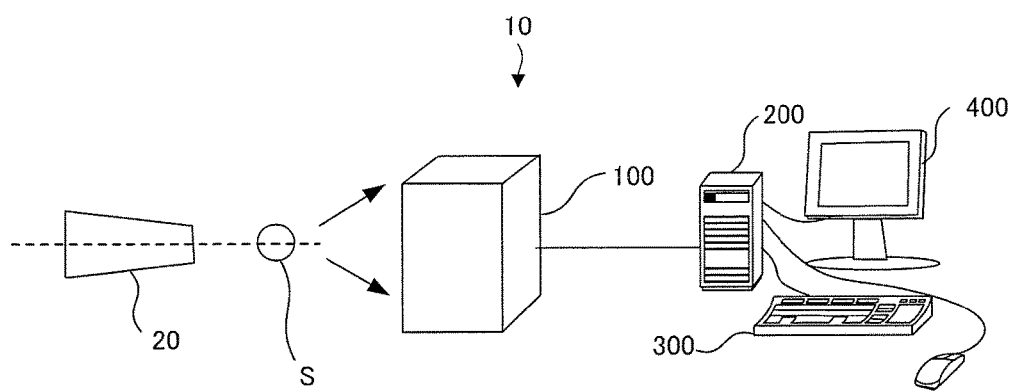
FIG. 1 is a schematic diagram showing the configuration of an X-ray diffraction system of the present invention.

Next, an embodiment of the present invention will be described with reference to the accompanying drawings. For ease of understanding of the description, in each drawing, the same reference numeral is attached to the same component, and the repeated explanation thereof is omitted.

(Whole Configuration)

FIG. 1 is a schematic diagram showing the configuration of an X-ray diffraction system 10 capable of simultaneously measuring using a multiple wavelength radiation source. As shown in FIG. 1, the X-ray diffraction system 10 includes an X-ray source 20, a sample S, an X-ray detector 100, and an X-ray data processing apparatus 200.

The X-ray source 20 generates an X-ray, for example, by causing an electron beam, which is emitted from a filament that is a cathode, to collide with a rotor target that is an anticathode. The X-ray emitted from the X-ray source 20 is the so-called point-focused X-ray beam having a circular or rectangular dotted cross-sectional shape.

On the circumference surface of the rotor target, there is provided a plurality of types of metals (e.g., Mo and Cu) of different atomic numbers. When an electron collides with a Cu target, an X-ray containing a CuKα ray (the wavelength is 1.542 Å) that is a characteristic ray is emitted, while when an electron collides with an Mo target, an X-ray containing an MoKα ray (the wavelength is 0.711 Å) that is a characteristic ray is emitted. In the X-ray emitted from the rotor target, the CuKα ray and MoKα ray which are the characteristic X-rays of different target materials are mixed.

The sample S is supported by a sample support device. The sample support device includes a simple support stand without a movable part, a three-axis goniometer, a four-axis goniometer, or the like. The sample support device is determined in accordance with the characteristics of the sample S and the type of measurement. The X-ray detector 100 detects a diffraction X-ray diffracted by the sample S. The X-ray data processing apparatus 200 processes X-ray diffraction data of the measured diffraction X-ray and displays the measurement result. The details of the X-ray detector 100 and the X-ray data processing apparatus 200 are described later. Note that, although X-ray data to be processed may not be diffraction X-ray data, the X-ray data processing apparatus 200 is suitable for processing the diffraction X-ray data.

(Configuration of X-Ray Detector and X-Ray Data Processing Apparatus)

Figure 2:
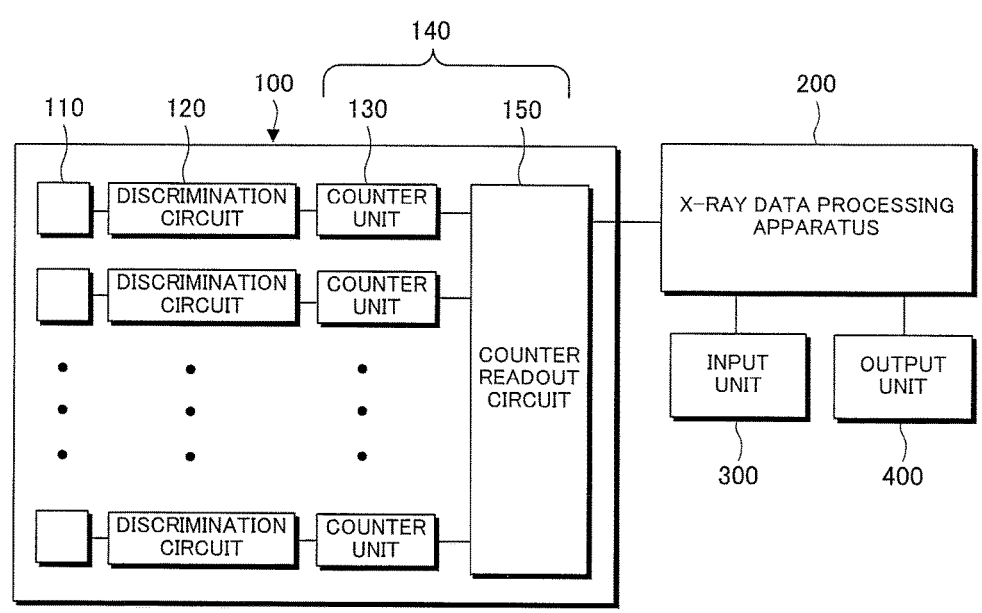
FIG. 2 is a block diagram showing mainly the configuration of an X-ray detector and an X-ray data processing apparatus.

FIG. 2 is a block diagram showing mainly the configuration of the X-ray detector 100 and the X-ray data processing apparatus 200. The X-ray detector 100 includes a plurality of X-ray receiving pixels 110, and is a two-dimensional semiconductor detector, for example. The plurality of pixels 110 is two-dimensionally arrayed and regularly arranged. Note that, the detector is not limited to the two-dimensional semiconductor detector, but may be a one-dimensional semiconductor detector.

A discrimination circuit 120 is individually connected to the plurality of pixels 110, and furthermore a counter unit 130 is individually connected to the discrimination circuit 120. A counter read-out circuit 150 is connected to each counter unit 130.

The discrimination circuit 120 discriminates and outputs a pulse signal of the pixel 110 for each X-ray wavelength. The counter unit 130 counts the respective numbers of the signals that are discriminated for each wavelength by the discrimination circuit 120. The counter unit 130 includes, for example, the same number of counter circuits as the number of discriminations so that the counter unit 130 can count the number of pulse signals that are discriminated by the discrimination circuit 120, respectively.

The output signal of the counter read-out circuit 150 is transmitted to the X-ray data processing apparatus 200 through a communication line. The X-ray data processing apparatus 200 is a personal computer, for example. The personal computer includes a CPU for calculation and control, a memory for storing data, system software stored in a predetermined region inside the memory, and application program software stored in other predetermined region inside the memory, and the like.

To the X-ray data processing apparatus 200, a keyboard or the like is connected as an input unit 300 that receives a user input. A user can, for example, display measurement results and instruct correction via the input unit 300. Moreover, an output unit 400, such as a display or a printer, is connected to the X-ray data processing apparatus 200. The output unit 400 outputs measurement results in accordance with an instruction from the X-ray data processing apparatus 200.

Figure 3A:
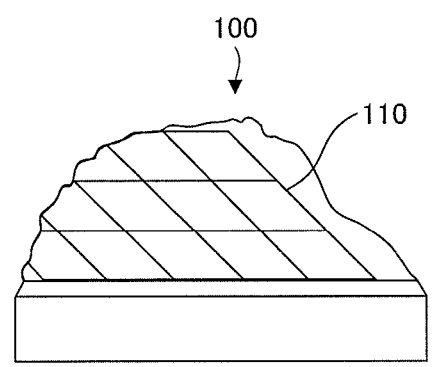
FIG. 3A is a perspective and cross-sectional view showing the structure of the X-ray detector.
Figure 3B:
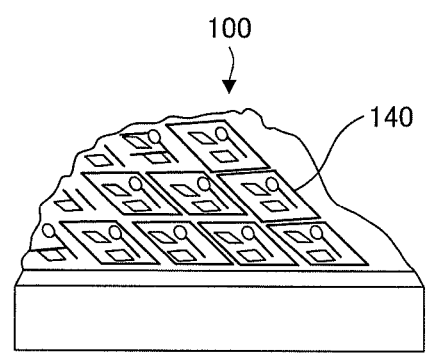
FIG. 3B is a perspective view and cross-sectional view showing the structure of the X-ray detector.
Figure 3C:
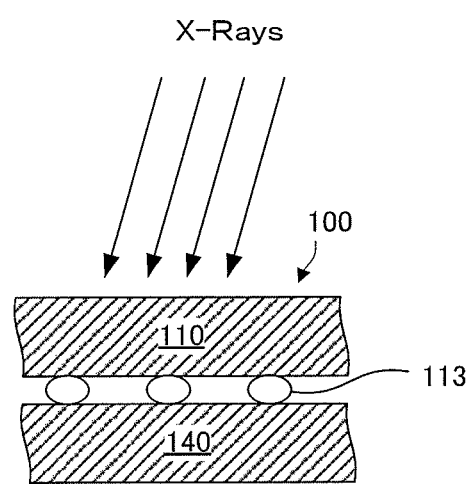
FIG. 3C is a perspective view and cross-sectional view showing the structure of the X-ray detector.

Each of FIG. 3A to FIG. 3C is the perspective and cross-sectional view showing the structure of the X-ray detector 100. As shown in FIG. 3A and FIG. 3B, the X-ray detector 100 includes the plurality of pixels 110 on the surface, and includes a read-out chip 140 on the back side of the pixel 110. Moreover, as shown in FIG. 3C, the pixel 110 and the read-out chip 140 are connected to each other by bump bonding 113. On the read-out chip 140, the discrimination circuit 120 and the counter unit 130 are mounted.

Figure 4:
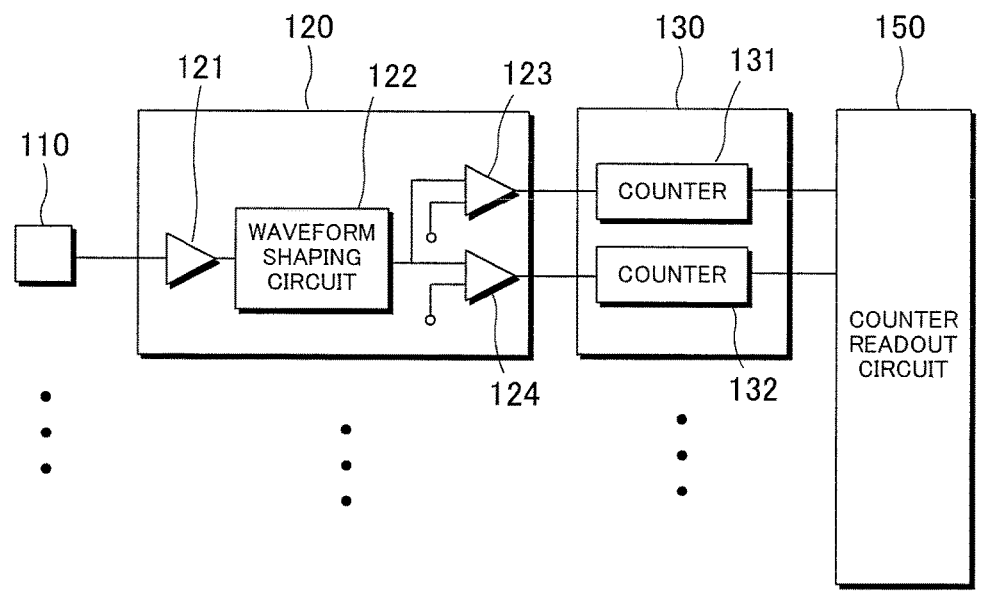
FIG. 4 is a block diagram showing the configuration of the X-ray detector.

FIG. 4 is a block diagram showing the configuration of the X-ray detector 100. Each of the plurality of pixels 110 is formed mainly from semiconductor, such as silicon, and outputs a pulse signal as an accumulation of the number of X-ray photons that are the charges generated in accordance with the wavelength (energy) of an X-ray. For example, each of the plurality of pixels 110, upon receipt of an X-ray photon of a CuKα ray, outputs a peak waveform of a wave height V1, while upon receipt of an X-ray photon of an MoKα ray, each of the plurality of pixels 110 outputs a peak waveform of a wave height V2. V1<V2 holds because the energy of the X-ray photon has a relation of CuKα<MoKα.

The discrimination circuit 120 is a circuit for discriminating, for each wavelength, the output signal of each pixel 110 that is output with a different wave height for each wavelength (i.e., for each energy) and outputs the resulting signal. The discrimination circuit 120 includes: an amplifier 121 for signal amplification; a waveform shaping circuit 122 that shapes a peak waveform to a peak waveform suitable for counters 131 and 132; and two comparators 123 and 124. Voltages Va and Vb are applied to a reference voltage terminal of each of the comparators 123 and 124, respectively.

The voltages Va and Vb have a relationship of V1<Va<V2 and Vb<V1. Accordingly, the comparator 123 outputs an output signal (MoKα ray) of the wave height V2 larger than Va. On the other hand, the comparator 124 outputs the both height V1 (CuKα ray) and height V2 (MoKα ray) which are larger than Vb.

The counter unit 130 includes the counters 131 and 132 connected to the individual output terminals of the comparators 123 and 124. Every time a signal is output to the output terminals of the comparators 123 and 124, the respective counters 131 and 132 count this output signal and outputs a count number within a predetermined time as an output signal. The counter 131 outputs a count number of the wave height V2, while the counter 132 outputs a count number obtained by adding a count number of the wave height V1 to the count number of the wave height V2.

The counter read-out circuit 150 determines the count number of the wave height V2 from the count number of the counter 131, and calculates the count number of the wave height V1 from a value obtained by subtracting the count number (V2) of the counter 131 from the count number (V1+V2) of the counter 132. Then, the counter read-out circuit 150 outputs how many pulses of the wave height V1 (CuKα ray) have been counted in the pixel 110 at a matrix address (i, j) and how many pulses of the wave height V2 (MoKα ray) have been counted in the pixel 110 at the matrix address (i, j). This output signal is transmitted to the X-ray data processing apparatus 200.

In this manner, the measurement data based on X-rays of different wavelengths can be simultaneously acquired by one measurement. Thus, waste of energy at the X-ray radiation source can be prevented, and exhaustion of the target in a short period of time can be prevented. Moreover, the measurement data based on each of the X-rays of different wavelengths can be acquired in a short period of time.

(Charge Sharing)

The charges (electrons or holes) that are generated during detection of a diffraction X-ray and then span the plurality of pixels 110 are detected as the data on a lower energy side. This phenomenon is referred to as charge sharing. Raw data transmitted from the X-ray detector 100 to the X-ray data processing apparatus 200 is affected by charge sharing.

Figure 5A:
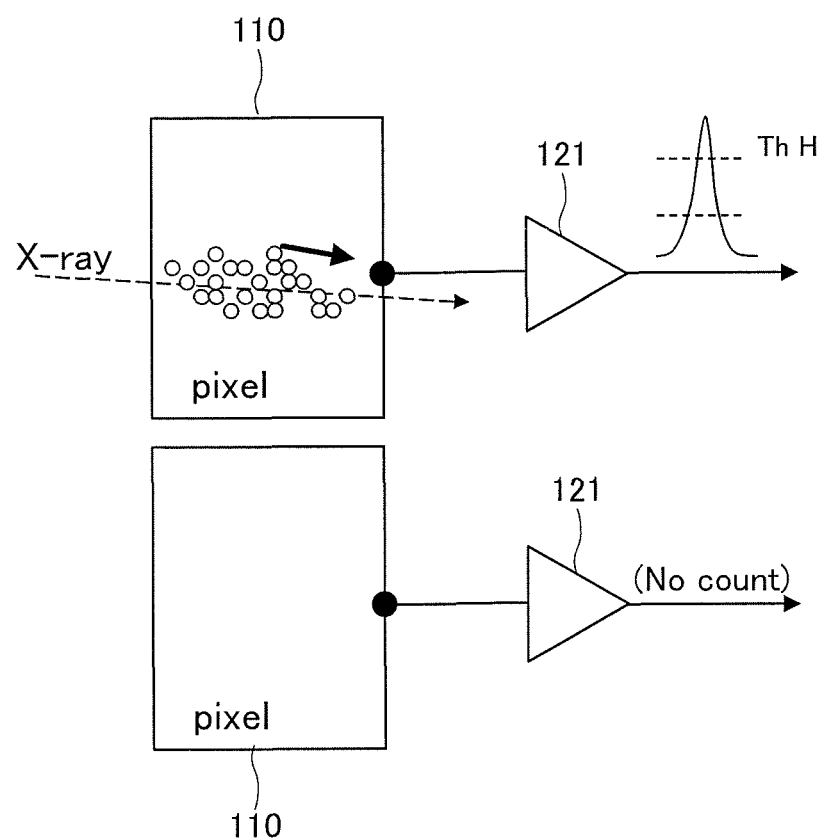
FIG. 5A is a schematic diagram showing the detection of an X-ray when charge sharing does not occur.
Figure 5B:
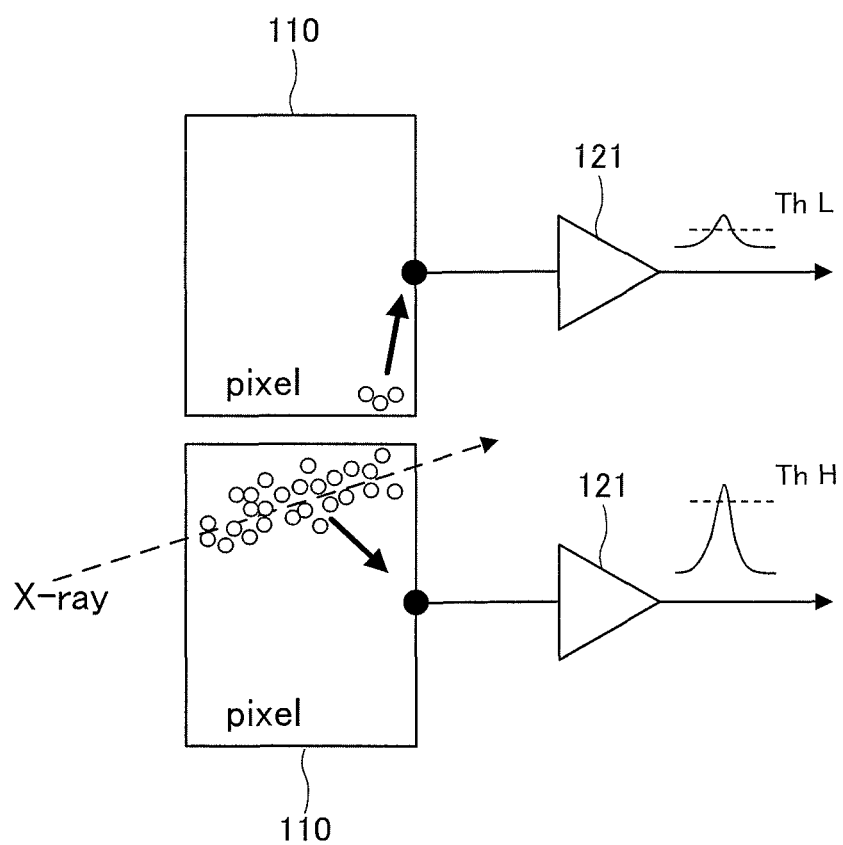
FIG. 5B is a schematic diagram showing the detection of an X-ray when charge sharing occurs.

FIG. 5A and FIG. 5B are schematic diagrams showing the detection of an X-ray when charge sharing does not occur and when charge sharing occurs, respectively. As shown in FIG. 5A, when an X-ray is incident only upon a single pixel 110, charge sharing does not occur and thus accurate measurement is possible. However, as shown in FIG. 5B, a cloud of charges generated in a vicinity of the surface of the X-ray detector 100 expands before reaching an electrode, resulting in charge sharing. Due to charge sharing occurring across two pixels 110, a peak detected by one pixel 110 is lowered and a low peak will be also detected by the other pixel 110.

Figure 6:
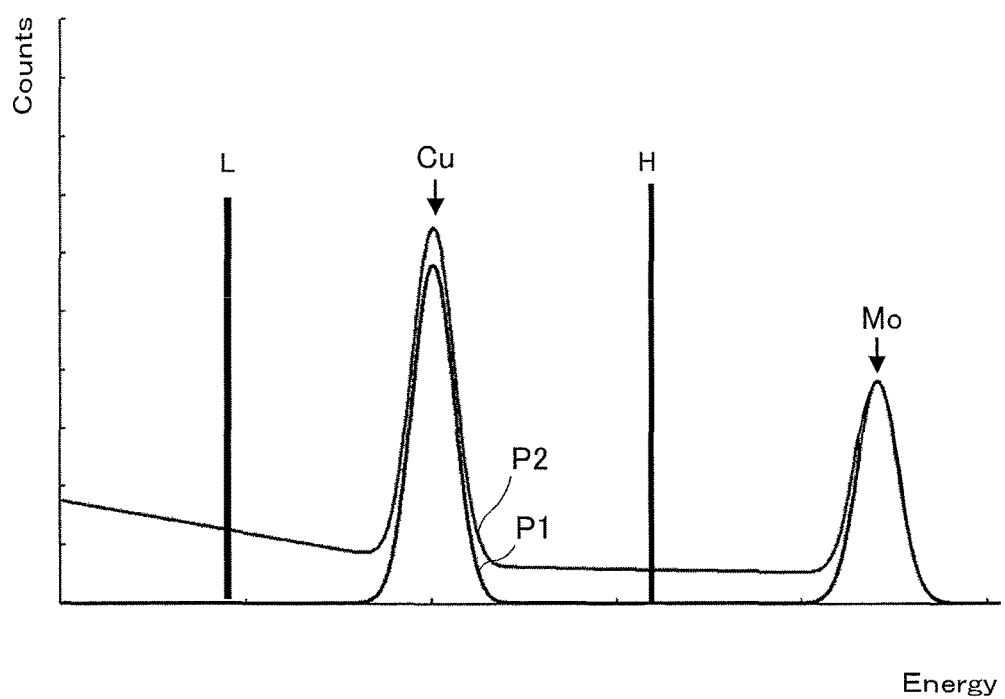
FIG. 6 is a view showing the measurement data when charge sharing does not occur and when charge sharing occurs.
Figure 7:
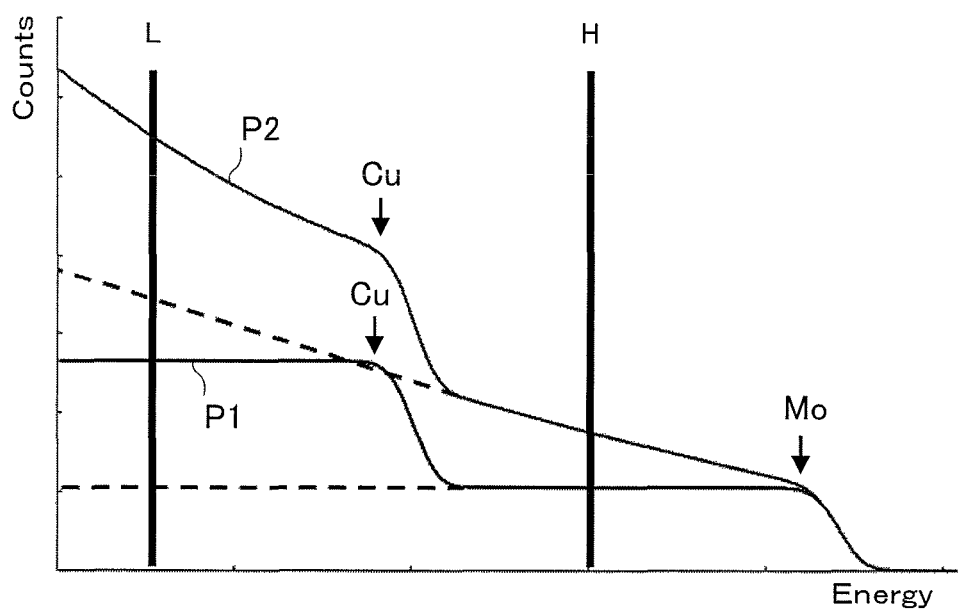
FIG. 7 is a view showing the measurement data (integrated value) when charge sharing does not occur and when charge sharing occurs.

Next, these are compared on measurement data. FIG. 6 is a view showing the measurement data when charge sharing does not occur and when charge sharing occurs. FIG. 7 is a view showing the measurement data (integrated value) when charge sharing does not occur and when charge sharing occurs. Data actually transmitted from the X-ray detector 100 is the integrated value as shown in FIG. 7.

In either of FIG. 6 and FIG. 7, ideal measurement data when charge sharing does not occur is represented by P1, and actual measurement data when charge sharing occurs is represented by P2. As compared with the ideal measurement data, the data between peaks of the actual measurement data is high by the charge sharing portion. Note that, H and L represent a threshold value on a higher side and a threshold value on a lower side, respectively, when the energy is discriminated in the discrimination circuit 120.

When the size of an X-ray is sufficiently smaller than the size of one pixel and the X-ray is incident only on a vicinity of the center of a pixel, the profile of P1 will be depicted. However, because the effect of charge sharing differs with the thickness of a sensor, the thickness also affects the profile.

(Configuration of X-Ray Data Processing Apparatus)

Figure 8:
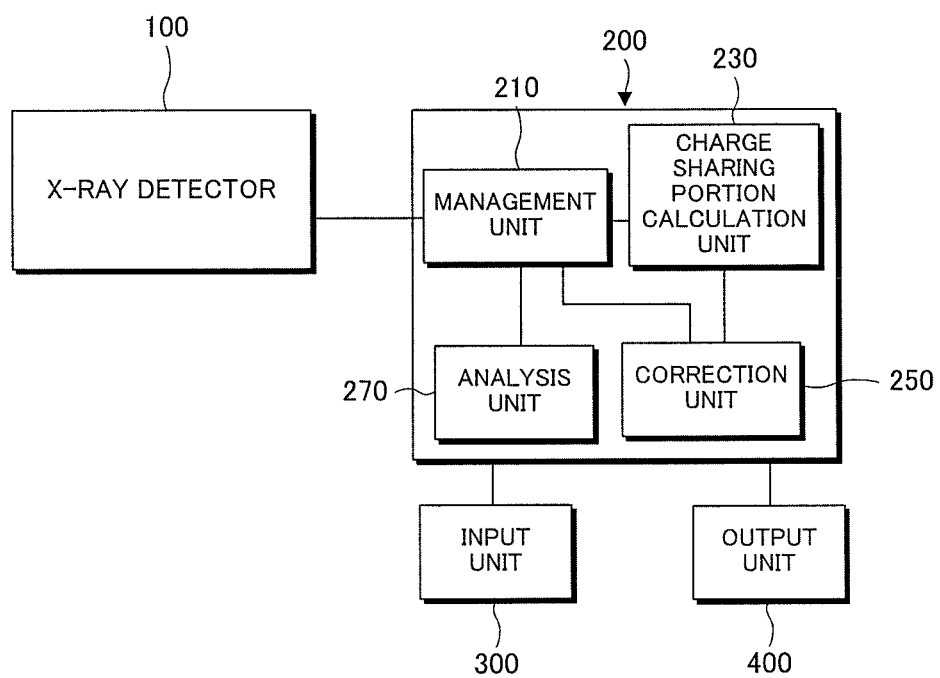
FIG. 8 is a block diagram showing mainly the configuration of the X-ray data processing apparatus.

FIG. 8 is a block diagram showing mainly the configuration of the X-ray data processing apparatus 200. The X-ray data processing apparatus 200 includes a management unit 210, a charge sharing portion calculation unit 230, a correction unit 250, and an analysis unit 270.

The management unit 210 receives and manages the X-ray diffraction data that is detected by the X-ray detector 100 and separated by the threshold value of energy. For example, the management unit 210 determines a diffraction X-ray intensity for each wavelength in association with the address (i, j) of the pixel 110, and stores the resulting data. The management unit 210 can, in accordance with an instruction of a user, cause the output unit 400 to display the data of both the diffraction images of a diffraction X-ray image of the Cu radiation source and a diffraction X-ray image of the Mo radiation source. The management unit 210 can display either one of the diffraction images, and can also display both of the images simultaneously.

The charge sharing portion calculation unit 230 calculates a detection amount caused by charge sharing, from the diffraction data present on a higher energy side of the X-ray diffraction data. From the diffraction data present on a higher energy side of the X-ray diffraction data, a detection amount caused by charge sharing is calculated. In this case, the charge sharing portion calculation unit 230 preferably calculates, for each pixel of a detector, a detection amount linked with charge sharing by overlapping a peak that is assumed to be detected due to the charge sharing that is generated from a peak present on a higher energy side. Thus, the effect by charge sharing can be evaluated more accurately than when evaluated by a linear function. Moreover, the X-ray profile shape due to charge share can be reproduced without depending on the shape and the like of a pixel. Note that the detail of the evaluation method of charge sharing is described later.

From a ratio, a difference, or the like between the diffraction data on a higher energy side present on a lower energy side and the diffraction data present on the lower energy side, the detection amount caused by charge sharing that relates to the higher energy side may be calculated.

Figure 9:
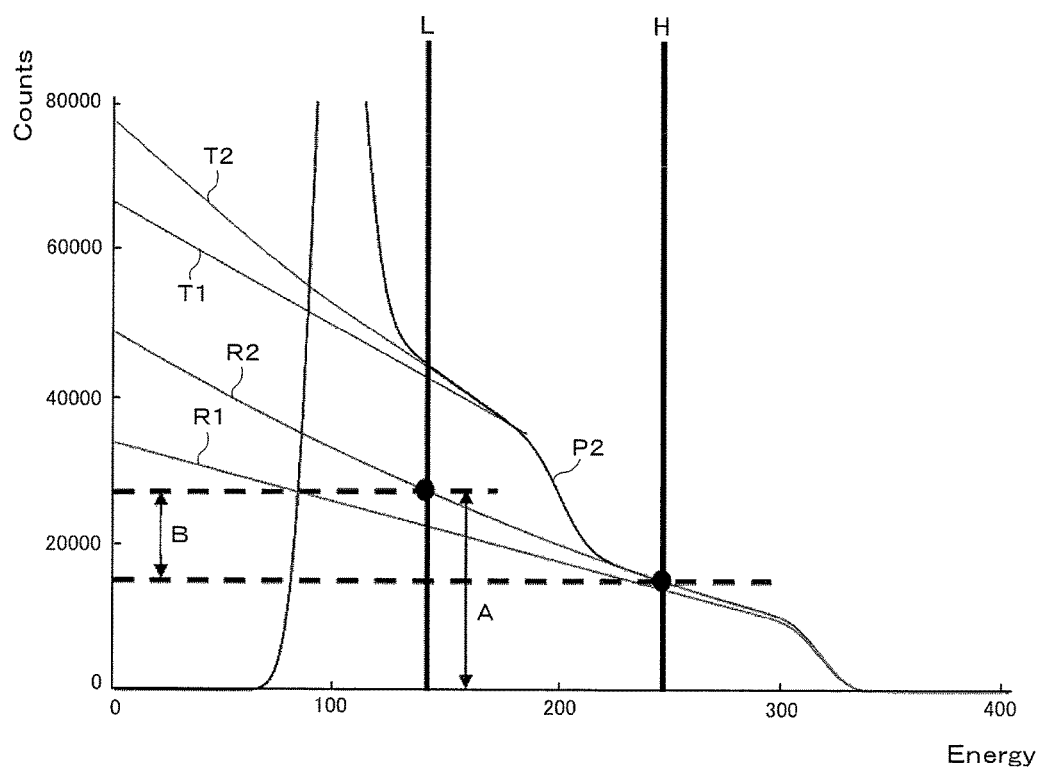
FIG. 9 is a view showing the measurement data (integrated value) when charge sharing occurs.

FIG. 9 is a view showing measurement data P2 (integrated value) when charge sharing occurs. With regard to the lower energy side data, characteristic data T2 that includes a charge sharing portion is shown as a curve with a large gradient (absolute value) relative to characteristic data T1 that does not include the charge sharing portion. Moreover, also with regard to the higher energy side data, characteristic data R2 that includes a charge sharing portion is shown as a curve with a large gradient (absolute value) relative to characteristic data R1 that does not include the charge sharing portion.

When X-rays of multiple wavelengths are incident upon the same pixel, a count A of a diffraction X-ray on a higher energy side included in lower energy side data cannot be calculated by simple subtraction of a detected value. When subtraction of a detected value is simply conducted, a count difference B including the detection amount caused by charge sharing serves as a remaining diffraction image on a lower energy side, but there are no measures to calculate this count difference B. Accordingly, when multiple wavelengths are incident inside the same pixel, the count A of the diffraction X-ray on a higher energy side included in the lower energy side data cannot be calculated.

In such a case, by calculating, from the higher energy side data, a ratio or a difference between a count C of the lower energy side data and the count A of the higher energy side data included in the count C of the lower energy side data, the count A of the higher energy side data included in the lower energy side data can be estimated. For example, the count A of the higher energy side data can be estimated from the higher energy side data and a numerical value obtained from a formula, or from the characteristic data of each pixel that is prepared in advance by actual measurement.

The correction unit 250 reconfigures an image on the lower energy side by subtracting the calculated detection amount caused by charge sharing from the data on a lower energy side of the X-ray diffraction data. Thus, the detection amount caused by charge sharing can be canceled, and a residual image of an X-ray on a higher energy side remaining in data on a lower energy side can be removed. As a result, also in measurement using radiation sources of multiple wavelengths, the accuracy of analysis compares favorably with the accuracy of analysis in measurement using a single radiation source.

Moreover, the correction unit 250 calculates, from an actual measurement value, a detection amount caused by charge sharing and reconfigures an image on a lower energy side. Thus, the detection amount caused by charge sharing can be canceled, and the residual image of an X-ray on a higher energy side remaining on a lower energy side can be removed. Then, diffraction X-rays of multiple wavelengths can be simultaneously measured, and these wavelengths can be separated from the data inside a single pixel.

The analysis unit 270 calculates a relationship among the wavelength, diffraction angle, and intensity of a diffraction X-ray based on a position in the plane of the diffraction X-ray which the X-ray detector 100 detected, and on an intensity count value for each wavelength of the diffraction X-ray which the counter read-out circuit 150 calculated. That is, the X-ray data processing apparatus 200 calculates at what diffraction angle and at how many counts of intensity an X-ray of a specific wavelength diffracted. Thus, a profile representing a relationship between a diffraction angle and a diffraction intensity can be acquired for each wavelength of a diffraction X-ray and can be further displayed on the output unit 400.

(Operation of X-Ray Data Processing Apparatus)

The operation of the X-ray data processing apparatus 200 configured as described above is described. First, the X-ray data processing apparatus 200 receives the X-ray diffraction data that is detected by the X-ray detector 100 and separated by a threshold value of energy. Then, the X-ray data processing apparatus 200 calculates a detection amount caused by charge sharing that is generated from a peak present on a higher energy side of the X-ray diffraction data. Next, the X-ray data processing apparatus 200 subtracts the detection amount caused by charge sharing which is calculated from the data on a lower energy side of the X-ray diffraction data. In this manner, a residual image of the X-ray on a higher energy side remaining in data on a lower energy side can be removed. Note that, using an actual measurement value prepared in advance, the detection amount caused by charge sharing may be subtracted from the data on a lower energy side of the diffraction data. In this manner, data on a lower energy side is reconfigured from the calculated detection amount caused by charge sharing.

Figure 10:
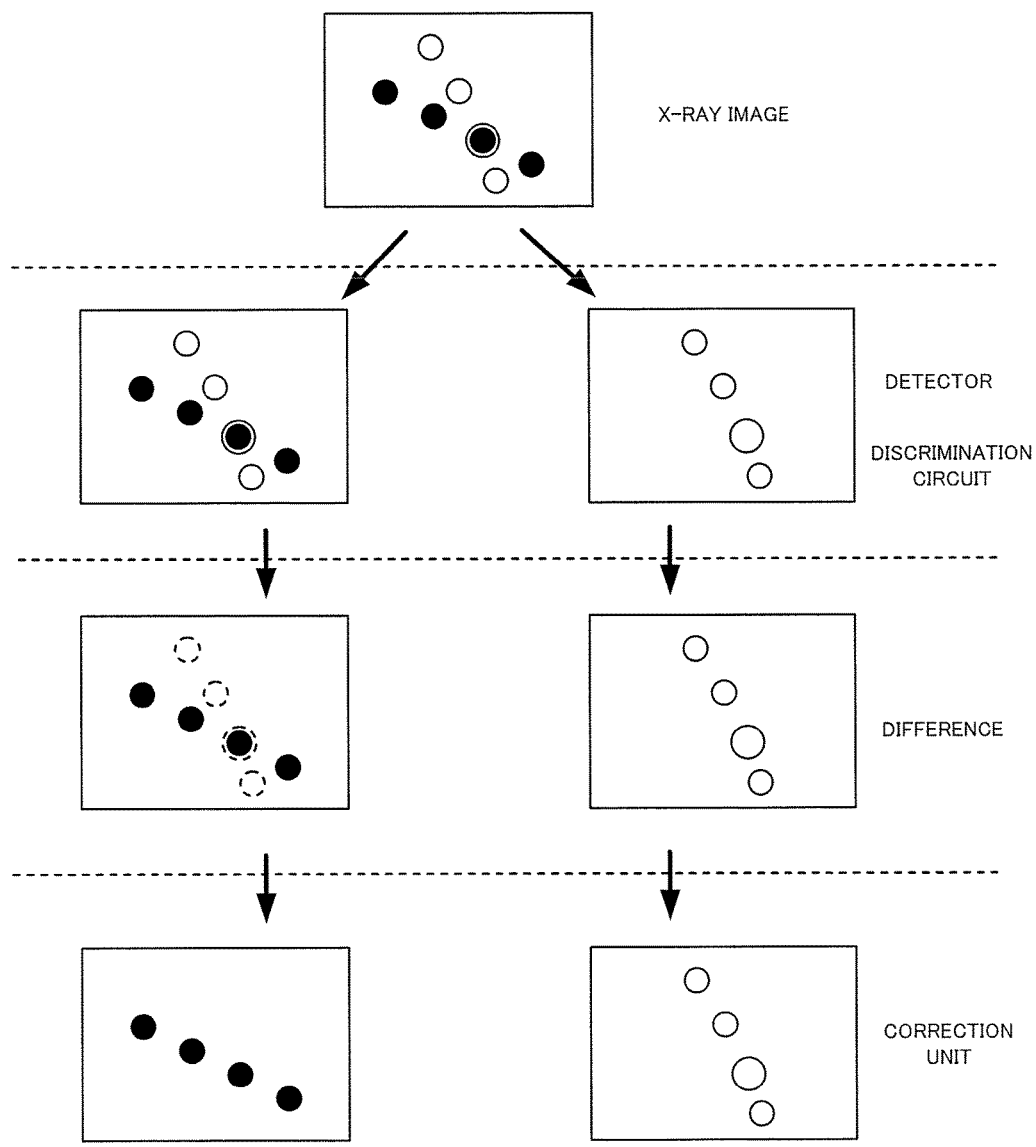
FIG. 10 is a schematic diagram showing a diffraction image at each stage.

FIG. 10 is a schematic diagram showing a diffraction image at each stage. Two images are output by discrimination by the discrimination circuit 120. After taking a difference of the two output images, a diffraction of Mo remains on the Cu image side (on a lower energy side). However, as described above, the residual image will disappear by calculating and correcting the detection amount caused by charge sharing. In this manner, the X-ray data processing apparatus of the present invention assumes that charge sharing occurs to data, instead of removing the effect of charge sharing during detection. Unless this method is used, a portion where a diffraction of high energy and a diffraction of low energy overlapped with each other cannot be separated. Diffractions that are not overlapped with each other can be separated even without using this method. Note that the operation of the X-ray data processing apparatus 200 as described above is performed by executing a program.

(Calculation Method of Detection Amount Caused by Charge Sharing)

Hereinafter, a calculation method of the detection amount caused by charge sharing is described. The X-ray detector 100 can simultaneously obtain diffraction data on a higher energy side and diffraction data on a lower energy side. From the obtained intensity ratio or difference between the diffraction data on a higher energy side present on a lower energy side and the obtained diffraction data present on a lower energy side, the X-ray data processing apparatus 200 calculates the detection amount of charge sharing events which are caused by higher energy X-ray, and corrects the X-ray diffraction data.

Note that, only with the diffraction data on a lower energy side, whether the diffraction data is the diffraction data on a higher energy side or the diffraction data on a lower energy side cannot be determined. Therefore, using the diffraction data on a higher energy side, a target pixel is identified, and with regard to this target pixel, a ratio or a difference is calculated. As a result, the detection amount caused by charge sharing can be calculated.

The examples of the method for evaluating accurate charge sharing from an X-ray intensity ratio or difference, include a method for fitting the detection amount caused by charge sharing to assumed diffraction data so that a solution of a formula passes through an estimated value calculated from the ratio or difference. By calculating the detection amount caused by charge sharing in this manner, such an effect is also obtained that an X-ray profile shape caused by charge sharing can be reproduced without depending on not only accurate evaluation but on the shape and the like of a pixel.

On the other hand, a method may be also used for calculating the detection amount caused by charge sharing using an actual measurement value that is prepared in advance. In this case, the detection amount caused by charge sharing is fit to assumed diffraction data so that an actual measurement value passes through an estimated value calculated from the ratio or difference.

(Method Using Formula)

A method for calculating the detection amount caused by charge sharing using the above-described formula is described. The X-ray data processing apparatus 200 calculates, from the diffraction data present on a higher energy side, the detection amount caused by charge sharing and corrects X-ray diffraction data.

At this time, as shown in Formula (1) below, there is also a method for evaluating as a linear function of a difference between the energy of a peak present on a higher energy side and a target energy. Note that the target energy is an energy with which the detection amount caused by charge sharing is attempted to be calculated.

$$I(E) = \left(1 - \text{erf}\left(\frac{E - E_{peak}}{\sqrt{2}\,\sigma}\right)\right) \times (A + B(E - E_{peak})) \, \ldots \quad \text{[Formula 1]}$$

$I(E)$: an intensity at a certain energy threshold value E of an X-ray profile
A, B: a real constant determined by an X ray intensity and the like
$E_{peak}$: an original peak energy not affected by charge share However, in order to evaluate the charge sharing, as shown in Formula (2), a method is preferable for superimposing, for each pixel of the X-ray detector 100, diffraction data that is assumed to be detected due to the charge sharing of diffraction data present on a higher energy side. By calculating the detection amount caused by charge sharing in this manner, such an effect is also obtained that an X-ray profile shape caused by charge sharing can be reproduced without depending on not only accurate evaluation but on the shape and the like of a pixel.

$$I(E) = A \int_0^{E_{peak}} p_{CS}(E_{CS}) \Delta S \left(1 - \text{erf}\left(\frac{E - E_{CS}}{\sqrt{2}\,\sigma}\right)\right) dE_{CS} + \quad \text{[Formula 2]}$$

$$B\left(1 - \text{erf}\left(\frac{E - E_{peak}}{\sqrt{2}\,\sigma}\right)\right) + C \, \ldots$$

$I(E)$: an intensity at a certain energy threshold value E of an X-ray profile
A, B, C: a real constant determined by an X ray intensity and the like
$E_{peak}$: an original peak energy not affected by charge share
$E_{cs}$: an apparent energy caused by charge share
$P_{cs}(E_{cs})$: a probability that a target pixel captures a charge corresponding to $E_{cs}$
$\Delta S$: the area of a region where an apparent energy caused by charge share varies by $\Delta E$ In the method of Formula (1), charge sharing is handled as a simple linear function, while in the method of Formula (2), integration is performed as superimposition of peaks each having a different center energy. For a target pixel, with a product of a probability $P_{cs}(E_{cs})$ that a charge of $E_{cs}$ is generated and a small area $\Delta S$ where the charge of $E_{cs}$ is generated when an X-ray is incident, an X-ray profile shape reflecting the detection amount caused by charge sharing can be reproduced without depending on the shape and the like of a pixel. With regard to a certain target pixel, $E_{cs}=0$ corresponds to a case where all the charges are captured by the neighboring pixels, while $E_{cs}=E_{peak}$ corresponds to a case where the target pixel captures all the charges.

As described above, in Formula (2), for each pixel of the X-ray detector 100, the detection amount caused by charge sharing is calculated assuming that the diffraction assumed to be detected occurs as a result and with a probability corresponding to the X-ray detector 100 and a diffraction present on a higher energy side. Thus, the effect by charge sharing can be accurately calculated using a probability that charges (electrons or holes) are generated.

Figure 11:
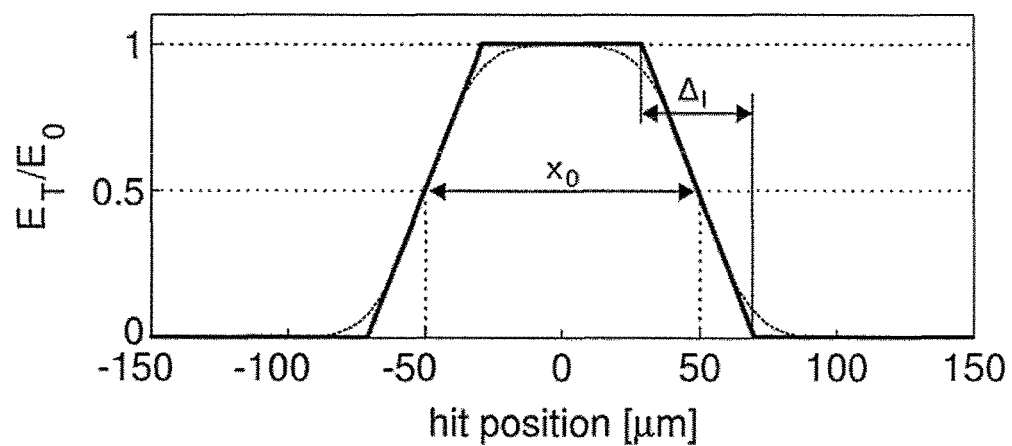
FIG. 11 is a graph showing an example of the relationship between a position and energy when charge sharing occurs.

FIG. 11 is a graph showing an example of the relationship between a position and energy when charge sharing occurs. FIG. 11 shows charge sharing when one pixel extends to 100 μm (from the position of −50 μm to the position of 50 μm). In this manner, the probability that the charges are generated for each pixel varies depending on the X-ray detector 100, and such an effect is evaluated in Formula (2).

In Formula (2), the detection amount caused by charge sharing is calculated by fitting a sum of an original intensity of a peak and the detection amount caused by charge sharing to actual diffraction data. Specifically, the coefficients A, B, and C in the formulas can be calculated by fitting.

Figure 12:
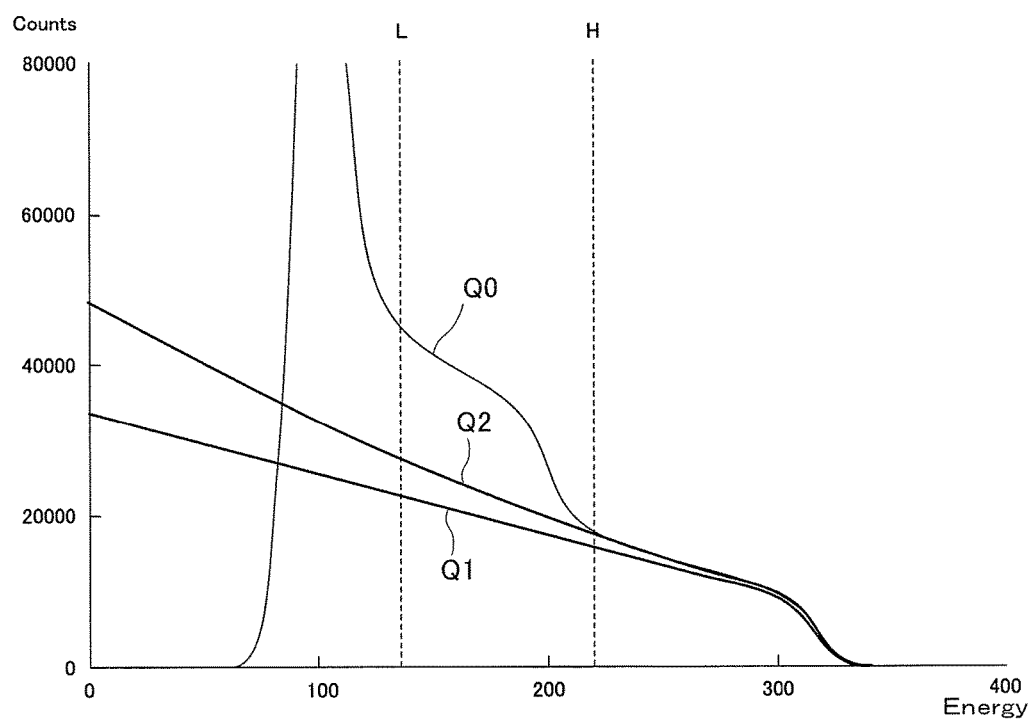
FIG. 12 is a graph for comparing the detection amounts caused by charge sharing that are calculated with respect to two methods.
Figure 13A:
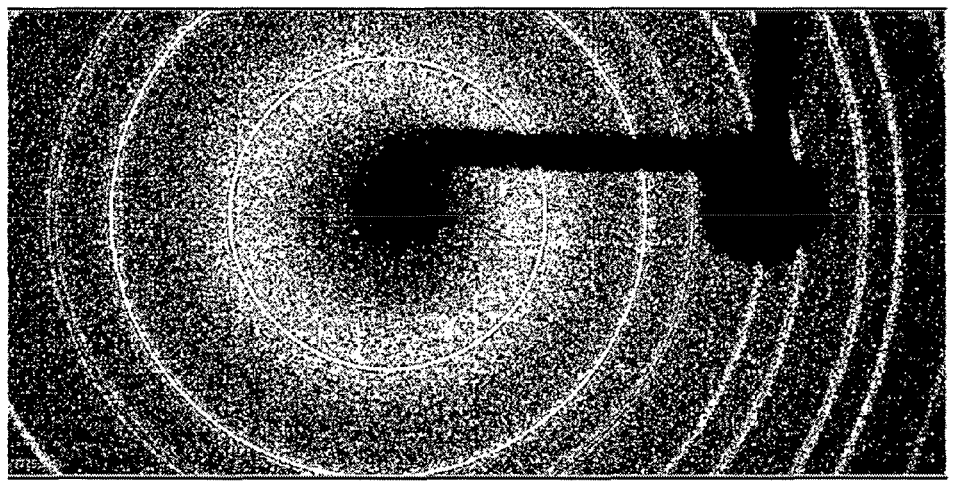
FIG. 13A is a view showing a diffraction image created by an Mo radiation source which is obtained by a conventional method.
Figure 13B:
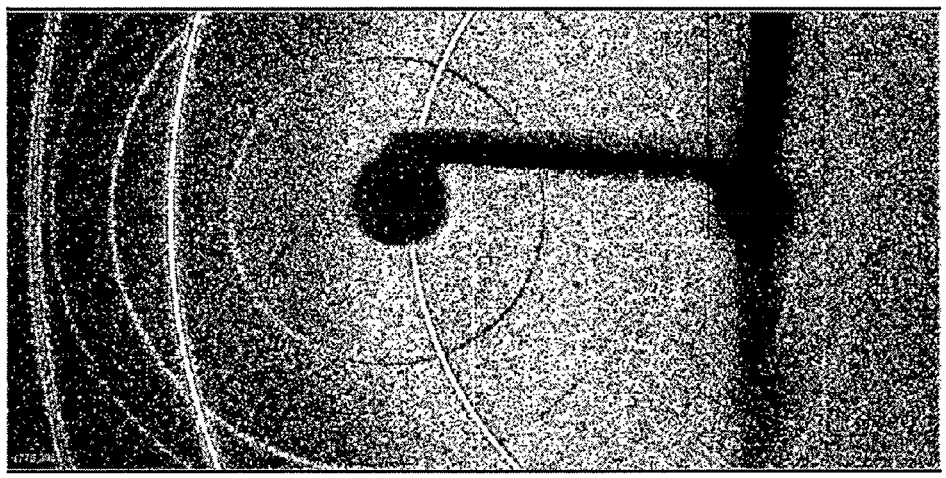
FIG. 13B is a view showing a diffraction image created by a Cu radiation source.

FIG. 12 is a graph for comparing the detection amounts caused by charge sharing which are calculated with respect to two methods. As shown in FIG. 12, a measurement value Q0 has an X-ray profile shape including two peaks (the Mo radiation source, the Cu radiation source), charge sharing, and electrical noise. When the Mo radiation source portion and the charge sharing portion thereof are evaluated by the method using Formula (1), a calculated value Q1 is obtained, where a deviation from the measurement value occurs on a lower energy side. On the other hand, when the Mo radiation source portion and the charge sharing portion thereof are evaluated by the method using Formula (2), a calculated value Q2 is obtained, which, even on a lower energy side, matches the measurement value Q0.

(In Cases where Three or More Types of Radiation Sources are Used)

In the above-described embodiment, two types of radiation sources of mainly Mo and Cu are used, but three or more types of radiation sources may be used. In this case, preferably, the charge sharing portion calculation unit 230, when there are two or more peaks on a higher energy side, for each pixel of a detector, superimposes peaks assumed to be detected due to the charge sharing that is caused from each of the peaks present on a higher energy side, adjusts an error accumulated for all the peaks present on a higher energy side, and calculates the detection amount caused by charge sharing. Thus, with regard to the measurement results by three or more types of radiation sources of different wavelengths, the charge sharing can be accurately evaluated.

What is claimed is:

1. An X-ray data diffraction system, comprising:
   one or more dimensional detectors simultaneously measuring incident X-rays of multiple wavelengths, the one or more dimensional detectors having a plurality of adjacent detection portions, the detector separating the measured incident X-rays for each of the detection portions by an energy threshold value; and
   an X-ray data processing apparatus that processes the measured incident X-rays,
   the X-ray data processing apparatus including:
   one or more processors executing a program correcting the measured incident X-rays, the program causes the one or more processors to:
      receive X-ray data detected by the one or more dimensional detectors;
      calculate a detection amount of charge sharing events in a lower energy side data, based on a higher energy side data obtained using a threshold value on a higher energy side and the lower energy side data obtained using a threshold value on a lower energy side of the received X-ray data, the charge sharing events being caused by higher energy X-ray; and reconfigure the lower energy side data using the calculated detection amount to cancel the detection amount caused by charge sharing for each of the plurality of adjacent detection portions to reduce an effect of the charge sharing event, wherein the detection amount of charge sharing events is calculated based on size of an area where the charge sharing can occur in each of the plurality of adjacent detection portions, and wherein the reconfigured lower energy side data is output to generate an image without a residual image.

2. The X-ray data diffraction system according to claim 1, wherein the program causes the one or more processors to calculate, for each detection portion of the detector, a detection amount caused by charge sharing, from a ratio or a difference between the higher energy side data included in the lower energy side data and the lower energy side data.

3. The X-ray data diffraction system according to claim 2, wherein the program causes the one or more processors to calculate, for each detection portion of the detector, a detection amount caused by charge sharing, with a probability corresponding to the detector and an incident X-ray wavelength.

4. The X-ray data diffraction system according to claim 2, wherein the program causes the one or more processors to calculate, for each detection portion of the detector, a detection amount caused by charge sharing, using an actual measurement value prepared in advance.

5. The X-ray data diffraction system according to claim 1, wherein the program causes the one or more processors to, when there are three or more types of incident X-ray energy, optimize an accumulated error and calculates the detection amount caused by charge sharing.

6. The X-ray data diffraction system according to claim 1, wherein the program causes the one or more processors to:

manage X-ray diffraction data that is measured with an Mo radiation source and a Cu radiation source and separated by a threshold value for separating each radiation source, calculate a detection amount caused by charge sharing, the charge sharing being linked with the Mo radiation source, and subtract the detection amount caused by charge sharing which is calculated from the X-ray diffraction data of the Cu radiation source.

* * * * *